United States Patent [19]

Meyer

[11] 4,276,188

[45] Jun. 30, 1981

[54] PROCESS FOR MANUFACTURING 2-STILBENYL-1,2,3-TRIAZOLES AND NEW 2-STILBENYL-1,2,3-TRIAZOLES

[75] Inventor: Hans R. Meyer, Binningen, Switzerland

[73] Assignee: Ciba-Geigy Corporation, Ardsley, N.Y.

[21] Appl. No.: 62,822

[22] Filed: Aug. 1, 1979

Related U.S. Application Data

[63] Continuation of Ser. No. 860,819, Dec. 15, 1977, abandoned, which is a continuation of Ser. No. 749,193, Dec. 9, 1976, abandoned, which is a continuation of Ser. No. 585,542, Jun. 10, 1975, abandoned.

[30] Foreign Application Priority Data

Jun. 12, 1974 [CH] Switzerland .......................... 8031/74
Jun. 12, 1974 [CH] Switzerland .......................... 8032/74

[51] Int. Cl.$^3$ ............................................. C07D 249/24
[52] U.S. Cl. ............................... 252/301.22; 427/158; 542/462; 542/463
[58] Field of Search ................... 542/463; 252/301.22; 427/158

[56] References Cited

U.S. PATENT DOCUMENTS

| | | | |
|---|---|---|---|
| 2,713,057 | 7/1955 | Zweidler et al. | 542/462 |
| 3,779,931 | 12/1973 | Fries et al. | 252/99 |
| 3,781,278 | 12/1973 | Siegrist et al. | 542/462 |

FOREIGN PATENT DOCUMENTS 211419  8/1955  Australia .
717889 11/1954  United Kingdom .

*Primary Examiner*—Arthur P. Demers
*Attorney, Agent, or Firm*—Edward McC. Roberts; John P. Spitals

[57] ABSTRACT

A new process for manufacturing 2-stilbenyl-1,2,3-triazoles as well as new 2-stilbenyl-1,2,3-triazoles and their use for the optically brightening of organic material are disclosed.

4 Claims, No Drawings

PROCESS FOR MANUFACTURING 2-STILBENYL-1,2,3-TRIAZOLES AND NEW 2-STILBENYL-1,2,3-TRIAZOLES

This is a continuation of application Ser. No. 860,819, filed Dec. 15, 1977, now abandoned, which is a continuation of Ser. No. 749,193, filed Dec. 9, 1976, now abandoned, which is a continuation of Ser. No. 585,542, filed June 10, 1975, now abandoned.

The present invention relates to a process for the manufacture of 2-stilbenyl-1,2,3-triazoles containing sulpho groups, new 2-stilbenyl-1,2,3-triazoles and the use thereof as optical brighteners.

Various processes for the manufacture of stilbene compounds are already known. One such process, which is widely applicable, has been disclosed under the name "anil synthesis" (compare, for example, Helvetica Chimica Acta 50, (1967) 906 et seq. and 52 (1969) 2521 et seq). Hitherto, however, the absence from the reactants of substituents capable of salt-formation, such as, for example, the sulphonic acid group, has been indicated as a condition for the anil synthesis to take place (compare Helvetica Chimica Acta 50 (1967) 912 and 52 (1969) 2524).

It has now been found, surprisingly, that 2-stilbenyl-1,2,3-triazoles containing sulpho groups can also be manufactured in good yields by means of the anil synthesis. This process makes possible a particularly advantageous method of manufacturing industrially important compounds.

The present invention accordingly relates to the process for the manufacture of 2-stilbenyl-1,2,3-triazoles of the formula

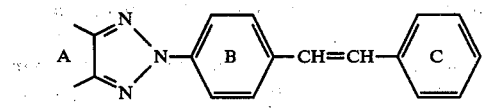
(1)

wherein A denotes a benzene, naphthalene or acenaphthene ring which is unsubstituted or has non-chromophoric substituents, the benzene nuclei B and C are unsubstituted or have nonchromophoric substituents, and the molecule contains at least one sulpho group, characterised in that a 2-tolyl-1,2,3-triazole of the formula

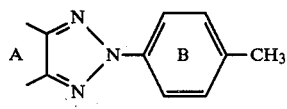
(2)

is reacted, in the presence of a strongly basic alkali metal compound in a, preferably strongly polar, neutral to basic organic solvent, with an anil of the formula

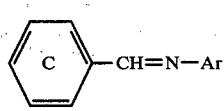
(3)

wherein Ar denotes an unsubstituted or substituted aromatic radical.

Examples of non-chromophoric substituents are alkyl having 1 to 4 carbon atoms, chlorine, bromine, alkoxy having 1 to 4 carbon atoms, phenoxy, alkylmercapto having 1 to 4 carbon atoms, phenylmercapto, carboxyl or sulpho or, in the case of two adjacent substituents, a methylenedioxy, trimethylene or tetramethylene group.

"Carboxyl" and "sulpho" are to be understood respectively as the radicals —COOM or —SO$_3$M wherein M represents hydrogen or a salt-forming cation. Suitable salt-forming cations M are, in general, those of alkaline earth metals, for example of calcium, barium or magnesium, and, particularly, of alkali metals, for example of sodium or potassium, but also ammonium, optionally substituted by alkyl or hydroxyalkyl having 1 to 4 carbon atoms, or amine salt ions of cyclic amines, such as pyridine, morpholine or piperidine. Besides hydrogen, the potassium cation and the sodium cation, in particular, are preferred in the meaning of M.

The aromatic radical Ar is, in general, made up of one or more six-membered carbocyclic structures, and it preferably denotes an unsubstituted or substituted naphthalene radical and, particularly, a phenyl radical which is unsubstituted or substituted by chlorine.

Within the scope of the present invention, the manufacture of 2-stilbenzyl-1,2,3-triazoles of the formula

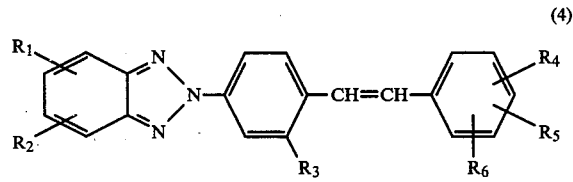
(4)

wherein $R_1$ denotes hydrogen, chlorine, alkoxy in the 5-position and having 1 to 4 carbon atoms, or phenoxy or, conjointly with $R_2$ in the 5,6-position denotes the methylenedioxy radical, or, conjointly with $R_2$ in the 6,7-position denotes the completion of a naphthalene ring which is unsubstituted or is substituted by a methoxy group or one or two sulpho groups, $R_2$ denotes hydrogen, or alkoxy in the 6-position and having 1 to 4 carbon atoms, or, conjointly with $R_1$ in the 5,6-position, denotes the methylenedioxy radical or, conjointly with $R_1$ in the 6,7-position, denotes the completion of a naphthalene ring which is unsubstituted or substituted by a methoxy group or one or two sulpho groups, $R_3$ denotes hydrogen, chlorine or sulpho, $R_4$ denotes hydrogen, chlorine, alkyl having 1 to 4 carbon atoms, alkoxy having 1 to 4 carbon atoms, phenyl, carboxyl or sulpho or, conjointly with $R_5$, denotes the trimethylene or tetramethylene radical, $R_5$ denotes hydrogen, alkoxy having 1 to 4 carbon atoms, chlorine or sulpho or, conjointly with $R_4$, denotes the trimethylene or tetramethylene radical, and $R_6$ denotes hydrogen or methoxy, and the molecule contains at least one, but not more than two sulpho groups, by reacting a 2-tolyl-1,2,3-triazole of the formula

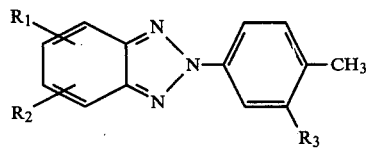
(5)

with an anil of the formula

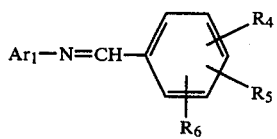
(6)

wherein $R_1$ to $R_6$ have the meaning indicated above, and $Ar_1$ denotes an unsubstituted or substituted phenyl or naphthyl radical, is of particular interest.

Emphasis should be given here, in particular, to the manufacture of 2-stilbenyl-1,2,3-triazoles, (a) of the formula

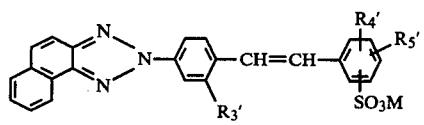
(7)

wherein $R_3'$ denotes hydrogen or sulpho, $R_4'$ denotes hydrogen, chlorine, alkyl having 1 to 4 carbon atoms, alkoxy having 1 to 4 carbon atoms, or sulpho, $R_5'$ denotes hydrogen, alkoxy having 1 to 4 carbon atoms, and M denotes hydrogen or a salt-forming cation, and the molecule contains at least one but not more than two sulpho groups, by reacting a 2-tolyl-1,2,3-triazole of the formula

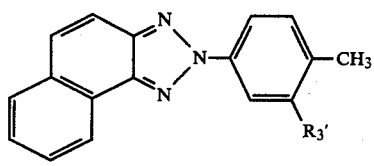
(8)

wherein $R_3'$ has the meaning indicated, with an anil of the formula

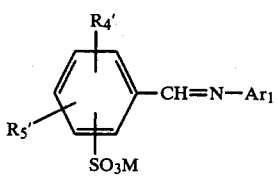
(9)

wherein $Ar_1$ denotes an unsubstituted or substituted phenyl or naphthyl radical, and $R_4'$ and $R_5'$ and M have the meaning indicated above, (b) of the formula

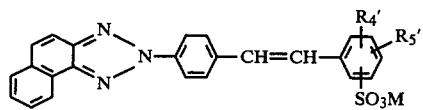
(10)

wherein $R_4'$, $R_5'$ and M have the meaning indicated above, by reacting a 2-tolyl-1,2,3-triazole of the formula

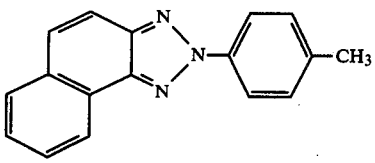
(11)

with an anil of the formula

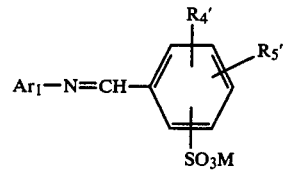
(12)

wherein $Ar_1$ denotes an unsubstituted or substituted phenyl or naphthyl radical, and $R_4'$, $R_5'$ and M have the meaning indicated above, (c) of the formula

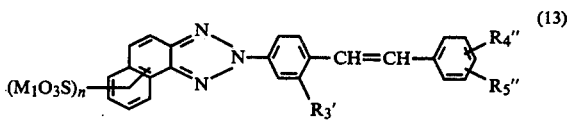
(13)

wherein n denotes the number 1 or 2, $R_3'$ denotes hydrogen or sulpho, $R_4''$ denotes hydrogen, chlorine, methoxy, not in the para-position, m-methyl, phenyl or carboxyl, $R_5''$ denotes hydrogen or methoxy, not in the para-position, and $M_1$ denotes a hydrogen ion, alkali metal ion, alkaline earth metal ion, ammonium ion or amine salt ion, and the molecule contains not more than two sulpho groups, by reacting a 2-tolyl-1,2,3-triazole of the formula

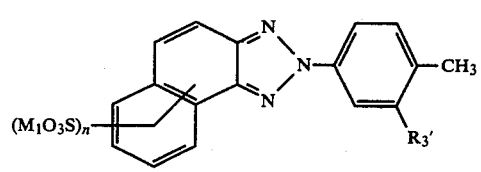
(14)

with an anil of the formula

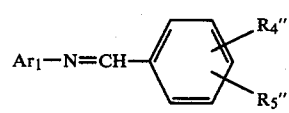
(15)

wherein $R_3'$, $R_4''$, $R_5''$, $M_1$ and n have the meaning indicated above, and $Ar_1$ denotes an unsubstituted or substituted phenyl or naphthyl radical, (d) of the formula

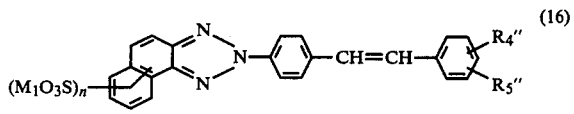
(16)

wherein R$_4''$, R$_5''$, M$_1$ and n have the meaning indicated above, by reacting a 2-tolyl-1,2,3-triazole of the formula

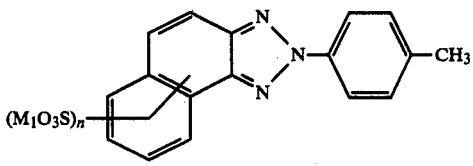 (17)

with an anil of the formula

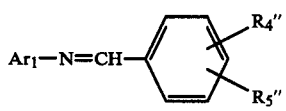 (18)

wherein R$_4''$, R$_5''$, M$_1$ and n have the meaning indicated above, and Ar$_1$ denotes an unsubstituted or substituted phenyl or naphthyl radical, (e) of the formula

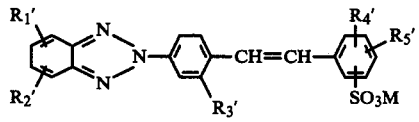 (19)

wherein R$_1'$ denotes hydrogen, chlorine, alkoxy in the 5-position and having 1 to 4 carbon atoms, or phenoxy or, conjointly with R$_2'$ in the 5,6-position, denotes the methylenedioxy radical, R$_2'$ denotes hydrogen, alkoxy in the 6-position and having 1 to 4 carbon atoms, or, conjointly with R$_1'$ in the 5,6-position, denotes the methylenedioxy radical, R$_3'$ denotes hydrogen or sulpho, R$_4'$ denotes hydrogen, chlorine, alkyl having 1 to 4 carbon atoms, alkoxy having 1 to 4 carbon atoms, or sulpho, R$_5'$ denotes hydrogen or alkoxy having 1 to 4 carbon atoms, and M denotes hydrogen or a salt-forming cation, and the molecule contains at least one but not more than two sulpho groups, by reacting a 2-tolyl-1,2,3-triazole of the formula

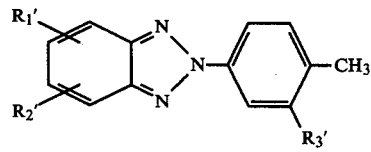 (20)

with an anil of the formula

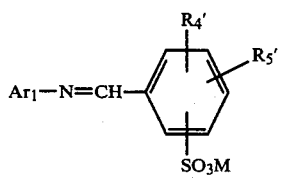 (21)

wherein R$_1'$ and R$_5'$ and M have the meaning indicated above and Ar$_1$ denotes an unsubstituted or substituted phenyl or naphthyl radical, and (f) of the formula

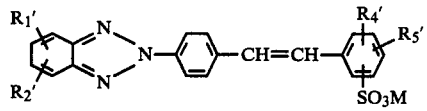 (22)

wherein R$_1'$, R$_2'$, R$_4'$, R$_5'$ and M have the meaning indicated above, and the molecule contains at least one but not more than two sulpho groups, by reacting a 2-tolyl-1,2,3-triazole of the formula

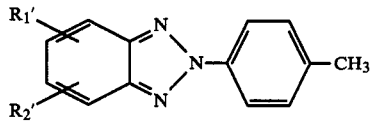 (23)

with an anil of the formula

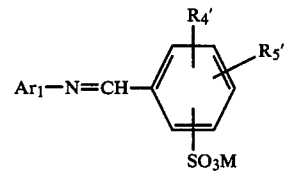 (24)

wherein R$_1'$, R$_2'$, R$_4'$, R$_5'$ and M have the meaning indicated above, and Ar$_1$ denotes an unsubstituted or substituted phenyl or naphthyl radical.

The starting materials for the manufacture of the compounds of the formulae (4), (7), (10), (13), (19) and (22) are known or can be manufactured in a manner which is in itself known.

The reaction with the anils can be carried out in the presence of a suitable, preferably strongly polar, neutral to alkaline, organic solvent which is free from atoms, particularly hydrogen atoms, which can be replaced by alkali metals. In practice, possible solvents of this kind are, above all, dialkylamides of formic acid and of phosphoric acid and tetraalkylureas, "alkyl" denoting a lower alkyl group containing 1 to 4 carbon atoms, particularly a methyl group. The following should be mentioned as important representatives of such solvents: diethylformamide, hexamethylphosphoric acid triamide, tetramethylurea and, especially, dimethylformamide. Mixtures of solvents can also be used.

Furthermore, as mentioned, a strongly basic alkali metal compound is necessary for the reaction.

Depending on the nature of the solvent used and the reactivity of the anil employed, certain sodium alcoholates such as sodium t-butylate, and, particularly, potassium compounds of the composition $$KOC_{m-1}H_{2m-1}$$ (25)

wherein m represents an integer from 1 to 6, preferably 2 to 6, such as, for example, potassium hydroxide or, particularly, potassium tert.-butylate, are suitable for this purpose. In the case of such alkali metal alcoholates, the reaction must be carried out in a virtually anhydrous medium, while in the case of potassium hydroxide, a small water content of up to about 15% is still allowable. Potassium hydroxide or sodium t-butylate is used advantageously, for example, in combination with hexamethylphosphoric acid triamide at elevated temperature, for example at 110°–130° C.

The 2-tolyl-1,2,3-triazoles are reacted with the anils in equivalent quantities. An excess of anil of up to about 25% is sometimes appropriate. It is advantageous to use at least an equivalent quantity of the alkali metal compound, that is to say at least 1 mol of a compound having, for example, a KO group, per one mol of anil. When potassium hydroxide is used, it is preferable to use a four-fold to eight-fold quantity. Particularly good yields are obtained when employing K tertiary butylate in a quantity which is one to six times, preferably two to four times, the equivalent quantity.

The reaction according to the invention can generally be carried out at temperatures in the range between about 10° and 150° C. With particularly reactive anils, the reaction takes place even at room temperature, in which case no external supply of heat is necessary. This is particularly advantageous if the reactants contain ring compounds or substituents which are easily opened or split off or modified chemically in some other way, by alkali. This is relevant, for example, to anils with chlorine substituents which can be split off easily. It is most advantageous, however, to carry out the reaction at elevated temperature, particularly when using sodium t-butylate or KOH. For example, the reaction mixture is warmed slowly to 30° to 80° C. and is then kept at this temperature for some time, for example ½ hour to 2 hours.

The manufacture of the anil and its reaction with the tolyl compound can also be carried out in a one-pot process. For example, an aldehyde is heated with excess aniline in dimethylformamide, the mixture is evaporated completely in vacuo, the totyl component and dimethylformamide are added and the customary procedure is followed. The end products can be worked up from the reaction mixture by customary methods which are in themselves known. Isolation is carried out, for example, by a precipitation with water or, in the case of water-soluble products, by salting-out, for example using NaCl or KCl, or by neutralisation or, where appropriate, by acidification with a strong mineral acid, such as, for example, HCl, it being possible in this last case to liberate the free sulphonic acids, if desired. These can be converted, if desired, into the corresponding alkali metal salts, alkaline earth metal salts, ammonium salts or amine salts, by reaction with alkali metal salts or alkaline earth metal salts or with ammonium hydroxide or amines. The amine salts of the sulphonic acids are also obtained, for example, by converting an alkali metal salt of the sulphonic acid into the sulphochloride by means of phosphorus oxychloride, thionyl chloride, phosphorus pentachloride and the like, and subsequent saponification in the presence of the desired amine.

The crude products are purified, as a rule, by extraction by boiling with chloroform and recrystallisation or extraction by boiling (depending on the solubility), for example with water, aqueous potassium chloride solution, n-propanol-water, ethylene glycol monomethyl ether, dimethylformamide, dimethylformamide-water, dimethylsulphoxide or dimethylsulphoxide-water.

It has become possible, in accordance with the process described above, to manufacture, in a simple manner, a considerable number of compounds which are in themselves known, but which have hitherto in part only been accessible by round-about routes.

The invention also relates to 2-stilbenyl-1,2,3-triazoles of the formula

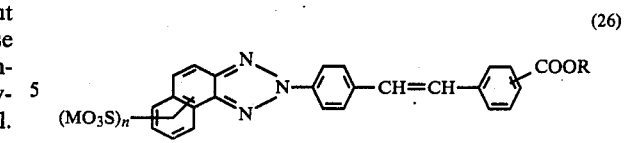

wherein R denotes hydrogen, a salt-forming cation, alkyl having 1 to 4 carbon atoms, alkyl having non-chromophoric substituents and 1 to 4 carbon atoms, or cyclohexyl, M denotes hydrogen or a salt-forming cation, and n denotes the number 1 or 2.

Within the scope of the formula (26), interest attaches above all to the compounds of the formula

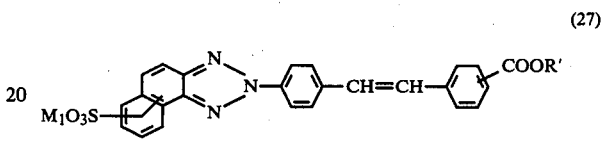

wherein R′ denotes hydrogen, an alkali metal ion, alkaline earth metal ion, ammonium ion or amine salt ion, or alkyl having 1 to 4 carbon atoms, and $M_1$ denotes a hydrogen ion, alkali metal ion, alkaline earth metal ion, ammonium ion or amine salt ion, and of the formula

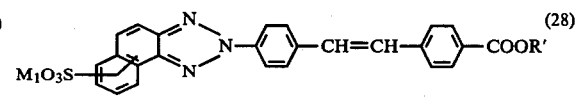

wherein R′ denotes hydrogen, an alkali metal ion, alkaline earth metal ion, ammonium ion or amine salt ion, or alkyl having 1 to 4 carbon atoms, and $M_1$ denotes a hydrogen ion, alkali metal ion, alkaline earth metal ion, ammonium ion or amine salt ion.

Compounds of particular practical interest correspond to the formula

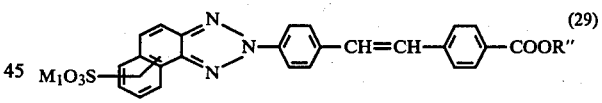

wherein R″ denotes alkyl having 1 to 4 carbon atoms, and $M_1$ denotes a hydrogen ion, alkali metal ion, alkaline earth metal ion, ammonium ion or amine salt ion, and of the formula

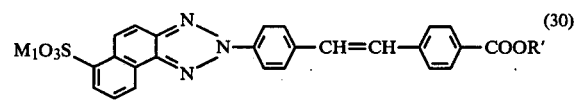

wherein R′ denotes hydrogen, an alkali metal ion, alkaline earth metal ion, ammonium ion or amine salt ion, or alkyl having 1 to 4 carbon atoms, and $M_1$ denotes a hydrogen ion, alkali metal ion, alkaline earth metal ion, ammonium ion or amine salt ion.

The 2-stilbenyl-1,2,3-triazoles of the formulae (26) to (30) are manufactured by the process according to the invention.

The carboxylic acid esters of the formulae (26) to (30) can be manufactured in a manner which is in itself known from the corresponding carboxylic acids by esterification. This is carried out, for example, by converting the carboxylic acids, by means of thionyl chloride or phosphorus oxychloride and the like, into the carboxylic acid chlorides and reacting the latter with alcohols. As a rule, the sulpho group is also chlorinated in the first stage, after which the sulpho chloride formed remains unchanged in the second stage. The corresponding sulphonic acid amine salts or sulphonic acid alkali metal salts of the carboxylic acid esters are then obtained in the subsequent saponification, in the presence of an amine, an amine derivative or stoichiometric quantities of an alkali metal base.

The compounds according to the invention, or compounds which can be manufactured in accordance with the invention, exhibit a more or less pronounced fluorescence in the dissolved or finely dispersed state. They can be used for optically brightening the most diverse synthetic, semi-synthetic or natural organic materials or substances which contain such organic materials. High effects with good fastness to light are achieved therewith on cellulose, cellulose having a synthetic resin finish and, particularly, on polyamides.

The following groups of organic materials, where optical brightening thereof is relevant, may be mentioned as examples of the above, without the survey given below being intended to express any restriction thereto:

I. Synthetic organic high-molecular materials:

(a) Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as for example, vinyl chloride, vinyl alcohol and vinylidene chloride);

(b) Polymerisation products such as are obtainable by ring opening, for example, polyamides of the polycaprolactam type, and also polymers which are obtainable both via polyaddition and via polycondensation, such as polyethers or polyacetals, (c) Polycondensation product or precondensates based on bifunctional or polyfunctional compounds possessing condensable groups, their homocondensation and co-condensation products, and after-treatment products, such as, for example, polyesters, especially polyesters which are saturated (for example ethylene glycol terephthalic acid polyester) or un-saturated (for example maleic acid-dialcohol polycondensates as well as their crosslinking products with copolymerisable vinyl monomers), unbranched or branched (also including those based on polyhydric alcohols, such as, for example, alkyd resins), polyesters, polyamides (for example hexamethylenediamine adipate), maleate resins, melamine resins, their pre-condensates and analogues, polycarbonates and silicones; and (d) Polyaddition products such as polyurethanes (cross-linked and non-crosslinked) and epoxide resins.

II. Semi-synthetic organic materials, for example, cellulose esters of varying degrees of esterification (socalled 2½-acetate or triacetate) or cellulose ethers, regenerated cellulose (viscose or cuprammonium cellulose), or their after-treatment products, and casein-plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, they is say, for example, predominantly three-dimensional bodies such as slabs, profiles, injection mouldings, various machined articles, chips, granules or foams, and also as predominantly two-dimensional bodies such as films, sheets, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkali or acid bath. The treatment is usually carried out at temperatures of about 20° to 140° C., for example at the boiling point of the bath or near it (about 90° C.). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

(a) Mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints.

(b) Mixed with so-called "carriers", wetting agents, plasticisers, swelling agents, anti-oxidants, light stabilisers, heat stabilisers and chemical bleaching agents (chlorite bleach or bleaching bath additives).

(c) Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or anti-microbial finishes.

(d) Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

(e) As additives to so-called "master batches".

(f) As additives to the most diverse industrial products in order to render these more marketable (for example improving the appearance of soaps, detergents and pigments).

(g) In combination with other optically brightening substances.

(h) In spinning bath preparations, that is to say as additives to spinning baths such as are used for improving the slip for the further processing of synthetic fibres, or from a special bath before stretching the fibre.

(i) As scintillators for various purposes of a photographic nature, such as, for example, for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or be combined in a single process stage.

The most of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 1 percent by weight and optionally of up to about 2 percent by weight can be employed. For most practical purposes, amounts between 0.0005 and 0.5 percent by weight are of preferred interest.

The new optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brighteners can be mixed, kneaded or ground with the detergent substances and, in the form, admixed to the finished washing powder. However, they can also be sprayed in a dissolved or pre-dispersed form onto the finished washing agent.

Suitable washing agents are the known mixtures of detergent substances such as, for example, soap in the form of chips and powders, synthetics, soluble salts of sulphuric acid half-esters of high fatty alcohols, arylsulphonic acids with higher and/or multiple alkyl substituents, sulphocarboxylic acid esters of medium to higher alcohols, fatty acid acylaminoalkyl- or acylaminoarylglycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The washing agents can further contain, for example: antistatic agents, skin protection agents which restore fat, such as lanolin, enzymes, anti-microbial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent, finished washing agent. Wash liquors which contain the indicated amounts of the optical brightener claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The textiles quoted are treated for 1 to 30 minutes at 20° to 100° C. in a wash liquor which contains 1 to 10 g/kg of a composite washing agent containing a builder and 0.05 to 1%, relative to the weight of washing agent, of the brighteners claimed. The liquor ratio can be 1:3 to 1:50. After washing, rinsing and drying are carried out as usual. The wash liquor can contain 0.2 g/l of active chlorine (for example as hypochlorite) or 0.1 to 2 g/l of sodium perborate, as a bleaching additive.

The compounds according to the invention, or compounds which can be manufactured in accordance with the invention, can also be used, depending on the substitution, as laser dyestuffs.

In the examples, unless otherwise specified, percentages are always percentages by weight. Unless otherwise noted, melting points and boiling points are uncorrected.

EXAMPLE 1

13.5 g of potassium t-butylate are introduced in portions into a solution of 10.8 g of the compound of the formula

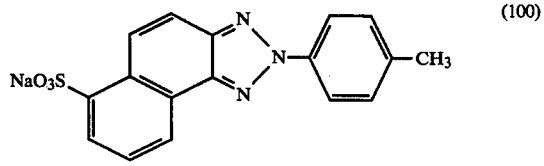

(100)

(92.4% strength) and 6.5 g of benzaldehyde p-chloroanil in 150 ml of anhydrous dimethylformamide at 75° C. while stirring well and passing nitrogen over the mixture. The temperature is kept at 80° C. for one hour, first by gentle cooling and then by warming. After cooling in an ice bath, 150 ml of water are added to the violet reaction mixture and the precipitated product is filtered off and washed with water until neutral. The dried, pulverised residue is extracted by boiling with 125 ml of toluene and the residue is filtered off at room temperature, washed with toluene and dried in vacuo at 110° C. This gives 12.2 g (about 90% of theory) of the compound of the formula

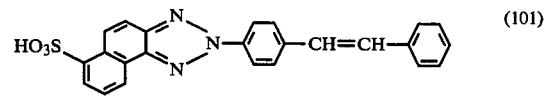

(101)

as the potassium salt, mixed with a little sodium salt, in the form of a pale yellow powder. It is recrystallised by being dissolved in 200 ml of boiling dimethylformamide, filtering the solution while hot together with 0.5 g of active charcoal and adding 90 ml of water to the hot filtrate. After cooling, filtering, washing with 1:1 dimethylformamide/water and methanol and drying, 9.9 g of pale yellow crystals are obtained.

If, instead of benzaldehyde p-chloroanil, the equivalent quantity of biphenyl-4-aldehyde p-chloroanil is used, the same procedure gives the potassium/sodium salt of the compound of the formula

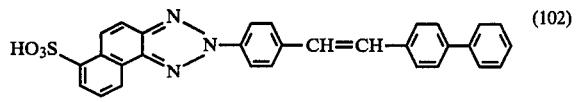

(102)

as a less readily soluble, pale yellow powder, which is recrystallised from dimethylsulphoxide.

EXAMPLE 2

13.5 g of potassium t-butylate are introduced into a solution of 11.7 g of the compound of the formula (100) [92.4% strength] and 8.5 g of the sodium salt of p-benzaldehydesulphonic acid anil (formula 106) in 360 ml of anhydrous dimethylformamide, while stirring vigorously and passing nitrogen over the mixture, a violet colouration being produced. The temperature is first kept at room temperature for ½ hour by gentle cooling and is then kept at 60° C. for ½ hour and at 80° C. for one hour, by warming. After cooling in an ice bath, 140 ml of distilled water are added and the mixture is neutralised with 3 ml of concentrated hydrochloric acid. The mixture is evaporated to dryness in a rotary evaporator and the residue is boiled up in 200 ml of distilled water. The cooled suspension is filtered and the residue is washed with three times 20 ml of 5% strength aqueous potassium chloride solution and dried in vacuo at 110° C. This gives 16.3 g (about 90% of theory) of the disulphonic acid of the formula

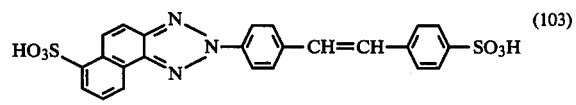

(103)

as the potassium salt, mixed with a little sodium salt. It is purified by being dissolved in 400 ml of distilled water, clarified by filtration after treatment with 0.5 g of active charcoal and crystallised by adding 530 ml of alcohol. After washing with 1:1 alcohol/water and drying, 10.2 g of a pale yellow powder are obtained.

The compound of the formula (100) required as the starting material is obtained as follows:

53.6 g of p-toluidine are dissolved in 125 ml of pure, concentrated hydrochloric acid and the mixture is poured into 1,500 ml of ice water. Diazotisation is then carried out at a temperature of 0° to 5° C. by adding a 30% strength aqueous solution of 34.6 g of sodium nitrite. After the addition of nitrite is completed, the mixture is stirred for a further ½ hour at 2° to 5° C. 111.6 g of 2-aminonaphthalene-5-sulphonic acid are separately dissolved in 1,500 ml of water at a pH value of 7.0, by adding sodium hydroxide solution, and the mixture is cooled to a temperature of 2° to 5° C. After the diazo solution has been added, the pH value is adjusted to 3.5 to 4.0 and is kept at this value until the coupling is completed, by dropwise addition of a concentrated, aqueous solution of sodium acetate. The mixture is then stirred for a further 12 hours at room temperature and the azo dyestuff is filtered off and washed with 500 ml of cold water. The moist dyestuff is then dissolved in a mixture of 1,000 ml of technical grade pyridine and 200 ml of water in a flask equipped with a stirrer and a reflux condenser, and a solution of 10 g of crystalline copper sulphate (pentahydrate) in 20 ml of water is added, followed by 20 g of sodium hydroxide as an aqueous, concentrated solution.

The reaction temperature is adjusted to 95° to 98° C. and a stream of air is passed into the mixture, with rapid stirring, during the whole period of the oxidation. The oxidation is complete after 10 to 12 hours. The copper salts are now removed by dropwise addition of 50 ml of an aqueous, approx. 18% strength solution of sodium sulphide and then adding 5 g of a filter aid material (for example Hy-flo Super Cel), heating again and clarifying by filtration. The filtrate is transferred to a steam distillation apparatus, 3 portions, each of 4 g, of concentrated hydrosulphite are added at the start of steam distillation and the pyridine is then driven off by means of steam. After the steam distillation has been completed, the contents of the flask are cooled and the product is precipitated as a whitish mass of crystals. This is filtered off, rinsed further with 500 ml of cold water and dried in vacuo at 100° to 105° C.

The sodium salt 2-(4-methylphenyl)-2H-naphtho-[1,2-d]-triazole-6-sulphonic acid is obtained as a whitish powder of a melting point above 300° C. The yield is 89.4% of theory, relative to 100% strength material.

If, in the preceding example, the 2-aminonaphthalene-5-sulphonic acid is replaced by 111.6 g of 2-aminonaphthalene-6-sulphonic acid or by 111.6 g of 2-aminonaphthalene-7-sulphonic acid or 111.6 g of 1-aminonaphthalene-4-sulphonic acid, the same procedure gives the sodium salt of 2-(4-methylphenyl)-2H-naphtho[1,2-d]-triazole-7-sulphonic acid or -8-sulphonic acid or -5-sulphonic acid.

Furthermore, the 2-aminonaphthalene-5-sulphonic acid can be replaced by 151.6 g of 2-aminonaphthalene-5,7-disulphonic acid or 151.6 g of 2-aminonaphthalene-4,8-disulphonic acid. The disodium salts of 2-(4-methylphenyl)-2H-naphtho-[1,2-d]triazole-6,8-disulphonic acid or of -5,9-disulphonic acid are obtained in this way, by an analogous process, as a whitish powder. These compounds are significantly more readily soluble in water than the abovementioned monosulphonic acids.

EXAMPLE 3

10.1 g of potassium t-butylate are introduced into a solution of 7.8 g of the compound of the formula

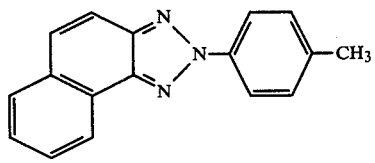

(104)

and 9.3 g of the sodium salt of p-benzaldehydesulphonic acid anil in 350 ml of dimethylformamide at 70° C., whilst stirring vigorously and passing nitrogen over the mixture. The mixture is kept at this temperature for one hour and is cooled in an ice bath and 100 ml of demineralised water are added. The precipitated product is filtered off, washed with three times 20 ml of water and dried in vacuo at 100° C. This gives 11.4 g of the compound of the formula

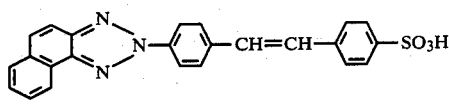

(105)

mainly as the potassium salt, mixed with a little sodium salt. It is purified by being extracted with chloroform and recrystallised from dimethylsulphoxide.

The sodium salt of p-benzaldehydesulphonic acid anil is obtained as follows: 62.5 g of the crude sodium salt of p-sulphobenzaldehyde are briefly boiled up in 500 ml of dimethylformamide and the solution is clarified by filtration at room temperature in order to remove insoluble salts. 28 g of aniline are added to the filtrate and it is heated to the boil for 10 minutes, in the course of which the anil already crystallises out. 200 ml of solvent are distilled off, the mixture is cooled and filtered and the residue is washed with 50 ml of dimethylformamide and with twice 50 ml of methanol. This gives 51.3 g of colourless crystals of the formula

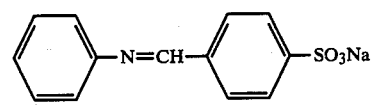

(106)

A further 7.4 g of nearly equally pure product are obtained by concentrating the filtrate to about ⅓ of its original volume.

EXAMPLE 4

The procedure followed is essentially in accordance with Example 1, 2 or 3, using corresponding 2-(p-tolyl)-naphthotriazoles and aldehyde anil derivatives, as well as 3 to 4 mols of potassium t-butylate per mol of 2-(p-tolyl)-naphthotriazole, and the compounds of the general formula (107) which are listed in Table I are obtained, mainly in the form of their potassium salts. In order to prepare the chlorine-containing compounds, the reaction is carried out at room temperature, 40° C. or 60° C. In order to prepare the compound of the formula (145), a larger excess of potassium t-butylate is used. When working up the compounds of the formulae (141) to (146), the reaction mixture is acidified with hydrochloric acid, after adding water, in order to liberate the free carboxylic acids.

The crude products are purified, as a rule, by extraction by boiling with chloroform and recrystallisation or extraction by boiling (depending on the solubility), for example with water, aqueous potassium chloride solution, n-propanol-water, ethylene glycol monomethyl ether, dimethylformamide, dimethylformamide-water, dimethylsulphoxide or dimethylsulphoxide-water.

(107)

TABLE I

| Formula No. | Substituents |
|---|---|
| (108) | 2-SO$_3$H |
| (109) | 3-SO$_3$H |

TABLE I-continued

| Formula No. | Substituents | |
|---|---|---|
| (110) | 6',8'-di SO₃H | |
| (111) | 5',9'-di SO₃H | |
| (112) | 6',8'-di SO₃H | 4-phenyl |
| (113) | 2''-SO₃H | |
| (114) | | 2-chloro-5-SO₃H |
| (115) | | 2,4-di-SO₃H |
| (116) | 5'-SO₃H | |
| (117) | 7'-SO₃H | |
| (118) | 8'-SO₃H | |
| (119) | 5'-methoxy | 3-SO₃H |
| (120) | | 2-methoxy-5-SO₃H |
| (121) | | 3-methyl-5-SO₃H |
| (122) | | 2,3-dimethoxy-5-SO₃H |
| (123) | 2'''-chloro- | 4-SO₃H |
| (124) | 6'-SO₃H | 4-chloro |
| (125) | 5'-SO₃H | 4-chloro |
| (126) | 7'-SO₃H | 4-chloro |
| (127) | | 4-chloro-3-SO₃H |
| (128) | 6'-SO₃H | 3-chloro |
| (129) | 6'-SO₃H | 2-chloro |
| (130) | 6'-SO₃H | 4-isopropyl |
| (131) | 6'-SO₃H | 3-methoxy |
| (132) | 6'-SO₃H | 3,4-tetramethylene |
| (133) | 6'-SO₃H | 3,4-trimethylene |
| (134) | 6'-SO₃H | 2-methoxy |
| (135) | 6'-SO₃H | 3,4-dichloro |
| (136) | 6'-SO₃H | 2,4-dichloro |
| (137) | 5',9'-di SO₃H | 4-chloro |
| (138) | 6',8'-di SO₃H | 4-chloro |
| (139) | 5'-SO₃H | 3-chloro |
| (140) | 5'-SO₃H | 2-chloro |
| (141) | 6'-SO₃H | 4-carboxy |
| (142) | 7'-SO₃H | 4-carboxy |
| (143) | 5'-SO₃H | 4-carboxy |
| (144) | 8'-SO₃H | 4-carboxy |
| (145) | 5',9'-di SO₃H | 4-carboxy |
| (146) | 6'-SO₃H | 2-carboxy |

Anil components:

The sodium salt of o-benzaldehydesulphonic acid anil required as the starting material of the formula (108), is obtained as follows: 208 g of the crude sodium salt of o-sulphobenzaldehyde are boiled up briefly in 1,040 ml of ethylene glycol monomethyl ether and the solution is clarified by filtration at room temperature in order to remove insoluble salts. 93.1 g of freshly distilled aniline are added to the filtrate and the mixture is heated for one hour at reflux temperature and filtered again from precipitated salts. 300 ml are now first distilled off at atmospheric pressure and then the remainder of the solvent is distilled off under reduced pressure. The residue is crystallised from one liter of n-butanol, filtered off and dried at 100° C. in vacuo. This gives 152 g of a colourless, hygroscopic product of the formula

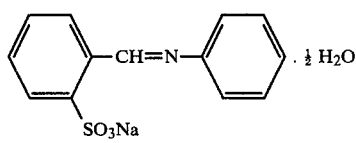

(after recrystallisation from n-butanol).

This anil is obtained in an even simpler manner by using, instead of ethylene glycol monomethyl ether, 1.2 l of n-butanol, from which it crystallises on cooling.

The sodium salt of m-benzaldehydesulphonic acid anil which is used for the preparation of the compounds of the formulae (109) or (119), is obtained in accordance with the instructions for the o-derivative. It is isolated by boiling up in alcohol (instead of in n-butanol) the residue obtained after the distillation of the solvent, and filtering off, at room temperature, the anil, which is insoluble therein, washing it with alcohol and drying it.

The potassium salt of 2,3-dimethoxy-5-sulphobenzaldehyde anil which is used as the starting material for the compound of the formula (122) is obtained by boiling 2,3-dimethoxy-5-sulphobenzaldehyde (K salt) with aniline (10% excess) in alcohol. The dilute solution is clarified by hot filtration, concentrated and cooled.

The potassium salt of 3-methyl-5-sulphobenzaldehyde anil, which is required as the starting material for the compound of the formula (121), is obtained in an analogous manner from 3-methyl-5-sulphobenzaldehyde (K salt).

The sodium salt of 4-chloro-3-sulphobenzaldehyde anil, which is required as the starting product for the compound of the formula (127), is obtained in an analogous manner from 4-chloro-3-sulphobenzaldehyde (Na salt).

The sodium salt of 2-chloro-5-sulphobenzaldehyde anil, which is required for the compound of the formula (114), is obtained in accordance with the instructions for the potassium salt of m-benzaldehydesulphonic acid anil.

The sodium salt of 2-methoxy-5-sulphobenzaldehyde anil, which is required for the compound of the formula (120), is obtained by boiling up 15.8 g of 2-methoxy-benzaldehydesulphonic acid (Na salt) in 100 ml of aniline and 23 ml of dimethylformamide, distilling off 30 ml of solvent and cooling.

The anil

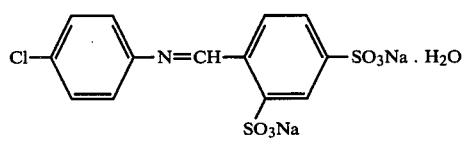

which is used for the preparation of the compound of the formula (115), is obtained by stirring benzaldehyde-2,4-disulphonic acid (disodium salt) in a 5-fold quantity of p-chloroaniline at 180° C. and evaporating the water formed. The thick mass is diluted with chloroform and filtered off. After washing with chloroform and drying, a sample of the residue is taken up in a large amount of hot alcohol and the solution is clarified by hot filtration, concentrated and cooled, whereupon the product precipitates.

EXAMPLE 5

The benzotriazoles of the formulae (147) to (153) are obtained, mainly in the form of their potassium salts, in a manner similar to that described in Example 2 to 4.

| | Formula No. | R₁ | R₂ | R₃ |
|---|---|---|---|---|
| 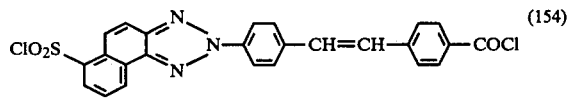 | (147) | SO₃H | H | H |
| | (148) | H | SO₃H | H |
| | (149) | H | H | SO₃H |
| 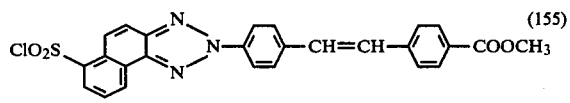 | (150) | SO₃H | H | H |
| | (151) | H | SO₃H | H |
| | (152) | H | H | SO₃H |
| 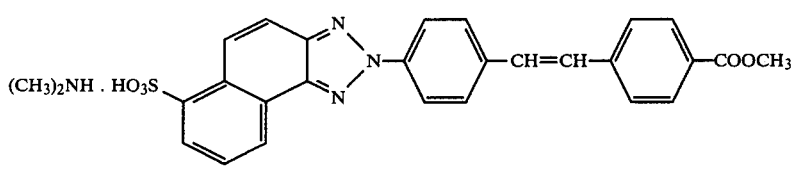 | (153) | H | H | SO₃H |

EXAMPLE 6

11.0 g of the crude compound of the formula (141) in 150 ml of chlorobenzene, 7 ml of thionyl chloride and 1 ml of dimethylformamide are heated under reflux for 2 hours. The solution is clarified by hot filtration, concentrated to one-half and cooled. After filtering and cooling, 4.7 g of the acid chloride of the formula $$ClO_2S\text{—[naphthotriazole]—N—[C}_6\text{H}_4\text{]—CH=CH—[C}_6\text{H}_4\text{]—COCl} \quad (154)$$

are obtained as light yellow crystals, melting point 244° C. (after recrystallisation from chlorobenzene).

3.3 g of the compound of the formula (154) in 50 ml of chlorobenzene and 0.8 ml of methanol are stirred under reflux for 2 hours. A further 9.2 ml of methanol are added and the mixture is heated under reflux for one hour more and allowed to cool. After filtering off, drying and washing with methanol, 3.1 g of the monoester of the formula $$ClO_2S\text{—[naphthotriazole]—N—[C}_6\text{H}_4\text{]—CH=CH—[C}_6\text{H}_4\text{]—COOCH}_3 \quad (155)$$

are obtained as pale yellow crystals, melting point 254° C.

2.7 g of the compound of the formula (155) in 20 ml of dimethylformamide and 1 ml of demineralised water are heated under reflux for ½ hour. The solution is evaporated to dryness in vacuo in a rotary evaporator and the residue is crystallised from water-n-propanol. After filtering off, washing with alcohol and drying, 1.6 g of the compound of the formula $$(CH_3)_2NH \cdot HO_3S\text{—[naphthotriazole]—N—[C}_6\text{H}_4\text{]—CH=CH—[C}_6\text{H}_4\text{]—COOCH}_3 \quad (156)$$

are obtained in the form of pale yellow crystals.

If the acid chloride of the formula (154) is esterified with ethanol, n-butanol or cyclohexanol, instead of methanol, and the procedure followed is otherwise as before, the corresponding dimethylamine salts of the methyl, ethyl, n-butyl or cyclohexyl esters are obtained.

The sulphonic acids of the formulae (157), (158) or (159) are obtained, in the form of their dimethylamine salts, in a similar manner from the carboxylic acids of the formulae (142), (143) or (144)

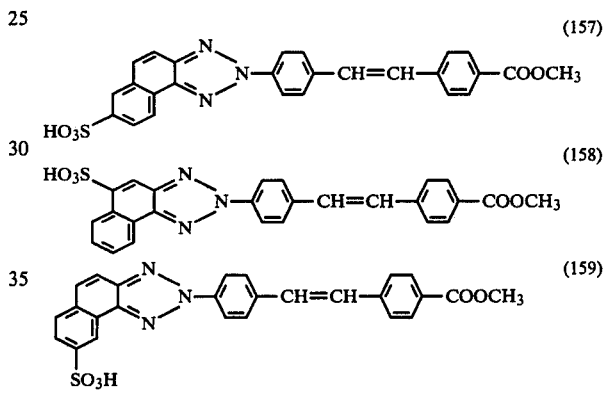

EXAMPLE 7

8.7 ml of a 10% strength aqueous potassium hydroxide solution are added to a suspension, at reflux temperature, of 10.65 g of the crude compound of the formula (141) in 100 ml of deionised water, a cloudy solution being formed. After adding 0.2 g of active charcoal, this solution is clarified by hot filtration and the filtrate is boiled up with 50 ml of 20% strength potassium hydroxide solution. The precipitated product is filtered off at room temperature and the residue is washed with 2.5% strength aqueous potassium hydroxide solution and dried. This gives 8.4 g of the pale yellow dipotassium salt of the formula $$KO_3S-\underset{N}{\overset{N}{\text{[naphtho-triazole]}}}N-\langle\text{phenyl}\rangle-CH=CH-\langle\text{phenyl}\rangle-COOK \quad (160)$$

EXAMPLE 8

A polyamide fibre fabric (Perlon-Helanca) is washed for 15 minutes, at a liquor ratio of 1:20, in a liquor warmed to 50° C. and containing the following additives per liter: 0.004 to 0.016 g of the brightener of the formula (156) 0.25 g of active chlorine (Javelle water) and 4 g of a washing powder of the following composition:
15.00% of dodecylbenzenesulphonate,
10.00% of sodium laurylsulphonate,
40.00% of sodium tripolyphosphate,
25.75% of anhydrous sodium sulphate,
7.00% of sodium metasilicate,
2.00% of carboxymethylcellulose and
0.25% of ethylenediaminetetraacetic acid.

The polyamide fibre fabric is not introduced into the wash liquor, warmed to 50° C., until 15 minutes after the preparation of the latter. After rinsing and drying, the fabric exhibits a good brightening effect.

The washing powder of the composition indicated above can also contain the brightener of the formula (156) indicated above, in a directly incorporated form.

EXAMPLE 9

Bleached cotton material is washed for 15 minutes, at a liquor ratio of 1:20, in a liquor warmed to 50° C. and containing the following additives per liter:
0.004 g of a brightener of the formula (156) or (160),
0.25 g of active chlorine (Javelle water) and
4 g of a washing powder of the following composition:
15.00% of dodecylbenzenesulphonate,
10.00% of sodium laurylsulphonate,
40.00% of sodium tripolyphosphate,
25.75% of anhydrous sodium sulphate,
7.00% of sodium metasilicate,
2.00% of carboxymethylcellulose and
0.25% of ethylenediaminetetraacetic acid.

The cotton material is not introduced into the wash liquor, warmed to 50° C., until 15 minutes after the preparation of the latter. After rinsing and drying, the fabric exhibits a good brightening effect with good fastness to chlorine.

The washing powder of the composition indicated above can also contain the brightener of the formula (156) in a directly incorporated form.

EXAMPLE 10

A polyamide fibre fabric (Perlon) is introduced, at a liquor ratio of 1:40 and at 60° C., into a bath which contains (relative to the weight of the material) 0.05% of a brightener of the formulae (156) or (160) and, per liter, 1 g of 80% strength acetic acid and 0.25 g of an addition reaction product of 30 to 35 mols of ethylene oxide with one mol of technical grade stearyl alcohol. The bath is warmed to the boil over the course of 30 minutes and is kept at the boil for 30 minutes. After rinsing and drying, a strong brightening effect, with good fastness to light, is obtained.

Similar effects are obtained if a brightener of the formulae (141), (142), (143), (144), (157), (158) or (159) is used.

Good brightening effects are also obtained if, instead of the fabric of polyamide 6, a fabric of polyamide 66 (nylon) is used.

Finally, it is also possible to work under high temperature conditions, for example for 30 minutes at 130° C. The addition of 3 g/l of hydrosulphite is advisable for this method of application.

EXAMPLE 11

10,000 g of a polyamide prepared in a known manner from hexamethylenediamine adipate are mixed, in the form of chips, in a tumbler for 12 hours with 30 g of titanium dioxide (rutile modification) and 5 g of the compound of the formula (156). The chips treated in this way are melted, after displacing the atmospheric oxygen by steam, in a kettle heated to 300° to 310° C. by means of oil or diphenyl vapour, and are stirred for half an hour. The melt is then extruded through a spinneret under a nitrogen pressure of 5 atmospheres gauge, and the filament spun in this manner is cooled and wound up on a spinning bobbin. The resulting filaments exhibit a good brightening effect.

Similarly good results are obtained if, instead of a polyamide prepared from hexamethylenediamine adipate, a polyamide prepared from $\epsilon$-caprolactam is used.

EXAMPLE 12

Bleached cotton material is washed for 30 minutes at 95° C. at a liquor ratio of 1:20. The wash liquor contains the following additives per liter:
0.004 g of a brightener of the formula (156) or (160) and 4 g of a washing powder of the following composition:
40.0% of soapflakes,
15.0% of sodium tripolyphosphate,
8.0% of sodium perborate,
1.0% of magnesium silicate,
11.0% of sodium metasilicate (9 $H_2O$),
24.6% of calcined sodium carbonate and
0.4% of ethylenediaminetetraacetic acid.

After rinsing and drying, the fabric has a strong brightening effect.

EXAMPLE 13

An article of cotton material, finished in a non-iron manner by means of aminoplast resin, is washed, at a liquor ratio of 1:20, for 15 minutes in a liquor warmed to 55° C. which contains the following additives per liter:
0.004 to 0.016 g of the brightener of the formula (156) and 4 g of a washing powder of the following composition:
15.00% of dodecylbenzenesulphonate,
10.00% of sodium laurylsulphonate,
40.00% of sodium tripolyphosphate,
25.75% of anhydrous sodium sulphate,
7.00% of sodium metasilicate,
2.00% of carboxymethylcellulose and
0.25% of ethylenediaminetetraacetic acid.

After rinsing and drying, the fabric exhibits a strong brightening effect with good fastness to light.

What I claim is:
1. A 2-stilbenyl-1,2,3-triazole of the formula

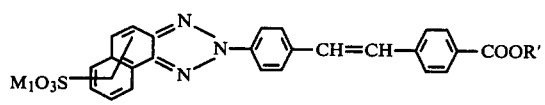

wherein R' denotes hydrogen, an alkali metal ion, alkaline earth metal ion, ammonium ion or amine salt ion or alkyl having 1 to 4 carbon atoms, and $M_1$ denotes a hydrogen ion, alkali metal ion, alkaline earth metal ion, ammonium ion or amine salt ion.

2. A 2-stilbenyl-1,2,3-triazole according to claim 1, of the formula

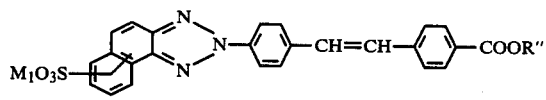

wherein R" denotes alkyl having 1 to 4 carbon atoms, and $M_1$ denotes a hydrogen ion, alkali metal ion, alkaline earth metal ion, ammonium ion or amine salt ion.

3. A 2-stilbenyl-1,2,3-triazole according to claim 1, of the formula

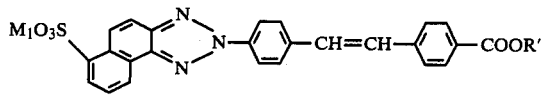

wherein R' denotes hydrogen, an alkali metal ion, alkaline earth metal ion, ammonium ion or amine salt ion or alkyl having 1 to 4 carbon atoms, and $M_1$ denotes a hydrogen ion, alkali metal ion, alkaline earth metal ion, ammonium ion or amine salt ion.

4. A process for optically brightening an organic material, which comprises incorporating into or applying to said material 0.0001 to 1 percent by weight, calculated on the total amount of the organic material, of a 2-stilbenyl-1,2,3-triazole, as defined in claim 1.

* * * * *